United States Patent
Sun

(10) Patent No.: US 12,000,837 B1
(45) Date of Patent: Jun. 4, 2024

(54) GRANULE FOR DETECTING PROTEIN IN PET URINE AND METHOD FOR PREPARING THE SAME

(71) Applicant: Shandong Ruida Silica Gel Co., Ltd., Linyi (CN)

(72) Inventor: Qinbin Sun, Linyi (CN)

(73) Assignee: SHANDONG RUIDA SILICA GEL CO., LTD., Linyi (CN)

( * ) Notice: Subject to any disclaimer, the term of this patent is extended or adjusted under 35 U.S.C. 154(b) by 0 days.

(21) Appl. No.: 18/516,927

(22) Filed: Nov. 21, 2023

(30) Foreign Application Priority Data

Aug. 2, 2023 (CN) .......................... 202310965005.7

(51) Int. Cl.
*G01N 33/68* (2006.01)
(52) U.S. Cl.
CPC .................................. *G01N 33/68* (2013.01)
(58) Field of Classification Search
CPC ....................................................... G01N 33/68
See application file for complete search history.

(56) References Cited

U.S. PATENT DOCUMENTS

2023/0276766 A1* 9/2023 Mu ...................... A01K 1/0155
119/171

FOREIGN PATENT DOCUMENTS

| CN | 109287499 A | * | 2/2019 | .......... A01K 1/0154 |
| CN | 114617069 A | * | 6/2022 | |
| KR | 20220090101 A | * | 6/2022 | |

OTHER PUBLICATIONS

English Espacenet Machine Translation of CN109287499. (Year: 2019).*
English Espacenet Machine Translation of KR20220090101. (Year: 2022).*
English Espacenet Machine Translation of CN114617069. (Year: 2022).*

* cited by examiner

*Primary Examiner* — Jennifer Wecker
*Assistant Examiner* — Kathryn Elizabeth Limbaugh
(74) *Attorney, Agent, or Firm* — MATTHIAS SCHOLL P.C.; Matthias Scholl

(57) ABSTRACT

A granule for detecting protein in pet urine comprises 60-80 parts by weight of silicone particles, 40-50 parts by weight of a filler, 10-20 parts by weight of an adhesive, 1-3 parts by weight of a bacteriostatic agent, 3-5 parts by weight of a deodorant, and 5-10 parts by weight of an tetrabromophenol blue indicator.

10 Claims, No Drawings

GRANULE FOR DETECTING PROTEIN IN PET URINE AND METHOD FOR PREPARING THE SAME

CROSS-REFERENCE TO RELATED APPLICATIONS

Pursuant to 35 U.S.C. § 119 and the Paris Convention Treaty, this application claims foreign priority to Chinese Patent Application No. 202310965005.7 filed Aug. 2, 2023, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to a granule for detecting protein in pet urine and a method for preparing the same.

Pets are good friends that bring happiness and companionship to people. However, pets are prone to diseases, and due to language barriers, when they suffer from serious symptoms, it may be difficult to find the pathogeny and treat. Protein content in the urine is an important indicator for health examination of pets. Some pet hospitals may provide checkup services for pets, but the hospitals are thinly distributed, and the fees are expensive.

SUMMARY

To solve the aforesaid problems, the disclosure provides a granule for detecting protein in pet urine and a method for preparing the same.

The granule for detecting protein in pet urine comprises 60-80 parts by weight of silicone particles, 40-50 parts by weight of a filler, 10-20 parts by weight of an adhesive, 1-3 parts by weight of a bacteriostatic agent, 3-5 parts by weight of a deodorant, and 5-10 parts by weight of an tetrabromophenol blue indicator.

In a class of this embodiment, the silicone particles are modified silicone particles, and are prepared as follows:
  a) ultrasonically cleaning the silicone particles in 30-40° C. water for 10-20 min, and further ultrasonically cleaning in industrial alcohol for 3-5 min, and drying;
  b) soaking the silicone particles treated in a) in silane coupling agent KH792 for 5-10 min, and drying at 50-60° C. in a drying oven; and
  c) soaking the silicone particles treated in b) in a mixed solution comprising polyethylene pyrrolidone, ethyl cellulose, N, N-dimethylformamide, ethyl acetate, and anhydrous ethanol for 10-15 min, and drying at 30-40° C., to yield modified silicone particles.

In a class of this embodiment, in c), a mass ratio of polyethylene pyrrolidone to ethyl cellulose to N, N-dimethylformamide to ethyl acetate to anhydrous ethanol is 1:0.2:5:1:10.

In a class of this embodiment, a particle size of the modified silicone particles is 1-2 mm.

In a class of this embodiment, the filler is modified starch, polyester fiber, acetate fiber, nylon fiber, microcrystalline cellulose, or a mixture thereof.

In a class of this embodiment, the adhesive is sodium carboxymethyl cellulose, pectin, guar gum, sodium alginate, xanthan gum, or a mixture thereof.

In a class of this embodiment, the bacteriostatic agent is polyhexamethylene biguanide hydrochloride, sodium benzoate, potassium sorbate, or a mixture thereof.

In a class of this embodiment, the deodorant is mugwort leaf, grapefruit peel, mulberry leaf, or a mixture thereof.

Further provided is a method for preparing the granule for detecting protein in pet urine comprising:
  1) crushing the silicone particles, the filler, the adhesive, the bacteriostatic agent, and the deodorant to particle size of 1-2 mm, and drying;
  2) dissolving tetrabromophenol blue in 0.1 mol/L NaOH solution, and diluting the NaOH solution containing dissolved tetrabromophenol blue with distilled water until a concentration of tetrabromophenol blue is 0.06% in the NaOH solution;
  3) soaking crushed silicone particles in the tetrabromophenol blue indicator for 30-40 min, and drying; and
  4) mixing the silicone particles treated in 3) and the filler, the adhesive, the bacteriostatic agent, and the deodorant treated in 1), feeding a resulting mixture to a tablet press machine for granulation, to yield flaky granules.

In a class of this embodiment, the complete flaky granules have a diameter of 30 mm, and a thickness of 4 mm.

The following advantages are associated with the granule for detecting protein in pet urine and a method for preparing the same:

When in use, the granule for detecting protein in pet urine of the disclosure comes into contact with pet urine. If the urine contains protein, the granule will change color, and the protein content in the urine can be determined by whether the color changes and the color level. Compared with existing technology, the granules of the disclosure can conveniently and accurately display whether pet urine contains proteins, help pet owners timely evaluate and manage their pet's health status, thus avoiding potential health risks.

DETAILED DESCRIPTION

To further illustrate the disclosure, embodiments detailing a granule for detecting protein in pet urine and a method for preparing the same are described below. It should be noted that the following embodiments are intended to describe and not to limit the disclosure.

Example 1

A granule for detecting protein in pet urine comprises: 60 parts by weight of silicone particles, 40 parts by weight of polyester fiber, 5 parts by weight of sodium carboxymethyl cellulose, 5 parts by weight of pectin, 1 part by weight of polyhexamethylene biguanidine hydrochloride, 3 parts by weight of mugwort leaf, and 5 parts by weight of tetrabromophenol blue indicator.

The silicone particles are modified silicone particles, which are prepared as follows:
  a) ultrasonically cleaning the silicone particles in 30° C. water for 20 min, and further ultrasonically cleaning in industrial alcohol for 3 min, and drying;
  b) soaking the silicone particles treated in a) in silane coupling agent KH792 for 5 min, and drying at 50° C. in a drying oven; and
  c) soaking the silicone particles treated in b) in a mixed solution comprising polyethylene pyrrolidone, ethyl cellulose, N, N-dimethylformamide, ethyl acetate, and anhydrous ethanol in a mass ratio of 1:0.2:5:1:10 for 10 min, and drying at 30° C., to yield modified silicone particles.

The disclosure also provides a method for preparing the granule for detecting protein in pet urine, the method comprising:
1) crushing the silicone particles, the filler, the adhesive, the bacteriostatic agent, and the deodorant to particle size of 1 mm, and drying;
2) dissolving tetrabromophenol blue in 0.1 mol/L NaOH solution, and diluting the NaOH solution containing dissolved tetrabromophenol blue with distilled water until a concentration of tetrabromophenol blue is 0.06% in the NaOH solution;
3) soaking crushed silicone particles in the tetrabromophenol blue indicator for 30 min, and drying; and
4) mixing the silicone particles treated in 3) and the filler, the adhesive, the bacteriostatic agent, and the deodorant treated in 1), feeding a resulting mixture to a tablet press machine for granulation, to yield flaky granules. The complete flaky granules have a diameter of 30 mm, and a thickness of 4 mm. The flaky granules are used to detect protein in pet urine.

Example 2

A granule for detecting protein in pet urine comprises: 80 parts by weight of silicone particles, 50 parts by weight of acetate fiber, 5 parts by weight of pectin, 5 parts by weight of guar gum, 5 parts by weight of sodium alginate, 5 parts by weight of xanthan gum, 2 parts by weight of polyhexamethylene biguanidine hydrochloride, 1 part by weight of sodium benzoate, 5 parts by weight of grapefruit peel, and 10 parts by weight of tetrabromophenol blue indicator.

The silicone particles are modified silicone particles, which are prepared as follows:
a) ultrasonically cleaning the silicone particles in 40° C. water for 10 min, and further ultrasonically cleaning in industrial alcohol for 5 min, and drying;
b) soaking the silicone particles treated in a) in silane coupling agent KH792 for 10 min, and drying at 60° C. in a drying oven; and
c) soaking the silicone particles treated in b) in a mixed solution comprising polyethylene pyrrolidone, ethyl cellulose, N, N-dimethylformamide, ethyl acetate, and anhydrous ethanol in a mass ratio of 1:0.2:5:1:10 for 15 min, and drying at 40° C., to yield modified silicone particles.

The disclosure also provides a method for preparing the granule for detecting protein in pet urine, the method comprising:
1) crushing the silicone particles, the filler, the adhesive, the bacteriostatic agent, and the deodorant to particle size of 2 mm, and drying;
2) dissolving tetrabromophenol blue in 0.1 mol/L NaOH solution, and diluting the NaOH solution containing dissolved tetrabromophenol blue with distilled water until a concentration of tetrabromophenol blue is 0.06% in the NaOH solution;
3) soaking crushed silicone particles in the tetrabromophenol blue indicator for 40 min, and drying; and
4) mixing the silicone particles treated in 3) and the filler, the adhesive, the bacteriostatic agent, and the deodorant treated in 1), feeding a resulting mixture to a tablet press machine for granulation, to yield flaky granules. The complete flaky granules have a diameter of 30 mm, and a thickness of 4 mm. The flaky granules are used to detect protein in pet urine.

Example 3

A granule for detecting protein in pet urine comprises: 70 parts by weight of silicone particles, 45 parts by weight of microcrystalline cellulose, 10 parts by weight of sodium carboxymethyl cellulose, 5 parts by weight of xanthan gum, 2 parts by weight of potassium sorbate, 4 parts by weight of grapefruit peel, and 8 parts by weight of tetrabromophenol blue indicator.

The silicone particles are modified silicone particles, which are prepared as follows:
a) ultrasonically cleaning the silicone particles in 35° C. water for 15 min, and further ultrasonically cleaning in industrial alcohol for 4 min, and drying;
b) soaking the silicone particles treated in a) in silane coupling agent KH792 for 8 min, and drying at 55° C. in a drying oven; and
c) soaking the silicone particles treated in b) in a mixed solution comprising polyethylene pyrrolidone, ethyl cellulose, N, N-dimethylformamide, ethyl acetate, and anhydrous ethanol in a mass ratio of 1:0.2:5:1:10 for 12 min, and drying at 35° C., to yield modified silicone particles.

The disclosure also provides a method for preparing the granule for detecting protein in pet urine, the method comprising:
1) crushing the silicone particles, the filler, the adhesive, the bacteriostatic agent, and the deodorant to particle size of 1 mm, and drying;
2) dissolving tetrabromophenol blue in 0.1 mol/L NaOH solution, and diluting the NaOH solution containing dissolved tetrabromophenol blue with distilled water until a concentration of tetrabromophenol blue is 0.06% in the NaOH solution;
3) soaking crushed silicone particles in the tetrabromophenol blue indicator for 35 min, and drying; and
4) mixing the silicone particles treated in 3) and the filler, the adhesive, the bacteriostatic agent, and the deodorant treated in 1), feeding a resulting mixture to a tablet press machine for granulation, to yield flaky granules. The complete flaky granules have a diameter of 30 mm, and a thickness of 4 mm. The flaky granules are used to detect protein in pet urine.

Example 4

A granule for detecting protein in pet urine comprises: 65 parts by weight of silicone particles, 42 parts by weight of modified starch, 13 parts by weight of odium carboxymethyl cellulose, 1.5 parts by weight of polyhexamethylene biguanide hydrochloride, 3.5 parts by weight of mugwort leaf, and 6 parts by weight of tetrabromophenol blue indicator.

The silicone particles are modified silicone particles, which are prepared as follows:
a) ultrasonically cleaning the silicone particles in 38° C. water for 13 min, and further ultrasonically cleaning in industrial alcohol for 4 min, and drying;
b) soaking the silicone particles treated in a) in silane coupling agent KH792 for 7 min, and drying at 53° C. in a drying oven; and
c) soaking the silicone particles treated in b) in a mixed solution comprising polyethylene pyrrolidone, ethyl cellulose, N, N-dimethylformamide, ethyl acetate, and anhydrous ethanol in a mass ratio of 1:0.2:5:1:10 for 14 min, and drying at 38° C., to yield modified silicone particles.

The disclosure also provides a method for preparing the granule for detecting protein in pet urine, the method comprising:

1) crushing the silicone particles, the filler, the adhesive, the bacteriostatic agent, and the deodorant to particle size of 2 mm, and drying;
2) dissolving tetrabromophenol blue in 0.1 mol/L NaOH solution, and diluting the NaOH solution containing dissolved tetrabromophenol blue with distilled water until a concentration of tetrabromophenol blue is 0.06% in the NaOH solution;
3) soaking crushed silicone particles in the tetrabromophenol blue indicator for 38 min, and drying; and
4) mixing the silicone particles treated in 3) and the filler, the adhesive, the bacteriostatic agent, and the deodorant treated in 1), feeding a resulting mixture to a tablet press machine for granulation, to yield flaky granules. The complete flaky granules have a diameter of 30 mm, and a thickness of 4 mm. The flaky granules are used to detect protein in pet urine.

Example 5

A granule for detecting protein in pet urine comprises: 75 parts by weight of silicone particles, 48 parts by weight of nylon fiber, 10 parts by weight of guar gum, 7 parts by weight of sodium alginate, 1 part by weight of sodium benzoate, 1.5 parts by weight of potassium sorbate, 4.5 parts by weight of mulberry leaves, and 9 parts by weight of tetrabromophenol blue indicator.

The silicone particles are modified silicone particles, which are prepared as follows:
a) ultrasonically cleaning the silicone particles in 32° C. water for 17 min, and further ultrasonically cleaning in industrial alcohol for 5 min, and drying;
b) soaking the silicone particles treated in a) in silane coupling agent KH792 for 9 min, and drying at 56° C. in a drying oven; and
c) soaking the silicone particles treated in b) in a mixed solution comprising polyethylene pyrrolidone, ethyl cellulose, N, N-dimethylformamide, ethyl acetate, and anhydrous ethanol in a mass ratio of 1:0.2:5:1:10 for 12 min, and drying at 36° C., to yield modified silicone particles.

The disclosure also provides a method for preparing the granule for detecting protein in pet urine, the method comprising:
1) crushing the silicone particles, the filler, the adhesive, the bacteriostatic agent, and the deodorant to particle size of 2 mm, and drying;
2) dissolving tetrabromophenol blue in 0.1 mol/L NaOH solution, and diluting the NaOH solution containing dissolved tetrabromophenol blue with distilled water until a concentration of tetrabromophenol blue is 0.06% in the NaOH solution;
3) soaking crushed silicone particles in the tetrabromophenol blue indicator for 40 min, and drying; and
4) mixing the silicone particles treated in 3) and the filler, the adhesive, the bacteriostatic agent, and the deodorant treated in 1), feeding a resulting mixture to a tablet press machine for granulation, to yield flaky granules. The complete flaky granules have a diameter of 30 mm, and a thickness of 4 mm. The flaky granules are used to detect protein in pet urine.

Comparison Example

The difference from Example 1 is that the silicone particles are not subject to modification treatment.

Experimental Results:

The experiments were conducted using the urine of pet cats. The urine of a normal pet cat was dropped onto the granules prepared in Example 1-5 of the disclosure, which was used as a control group to observe color changes. Take pet cat urine with protein content of 0.1 g/L albumin, 0.15 g/L albumin, 0.3 g/L albumin, 1.0 g/L albumin, and 3.0 g/L albumin and drop them onto the granules in Examples 1-5 as the experimental groups, and observe the color changes. Add tap water dropwise onto the granules in Examples 1-5 as a blank group, and observe the color changes. The results are shown in Table 1.

TABLE 1

| | | Experimental groups | | | | | | |
|---|---|---|---|---|---|---|---|---|
| | Items | 0.1 g/L albumin | 0.15 g/L albumin | 0.3 g/L albumin | 1.0 g/L albumin | 3.0 g/L albumin | Control group | Blank group |
| Example 1 | Color development and time | Color of the granules changes to light blue after 2 seconds | Color of the granules changes to blue after 2 seconds | Color of the granules changes to blue after 2 seconds | Color of the granules changes to blue after 2 seconds | Color of the granules changes to blue after 2 seconds | No change | No change |
| | Color level | / | +− | +1 | +2 | +3 | | |
| | Color persistence | 7 days | 7 days | 7 days | 7 days | 7 days | | |
| Example 2 | Color development and time | Color of the granules changes to light blue after 2 seconds | Color of the granules changes to blue after 2 seconds | Color of the granules changes to blue after 2 seconds | Color of the granules changes to blue after 2 seconds | Color of the granules changes to blue after 2 seconds | No change | No change |
| | Color level | / | +− | +1 | +2 | +3 | | |
| | Color persistence | 7 days | 7 days | 7 days | 7 days | 7 days | | |

TABLE 1-continued

| | | Experimental groups | | | | | | |
|---|---|---|---|---|---|---|---|---|
| Items | | 0.1 g/L albumin | 0.15 g/L albumin | 0.3 g/L albumin | 1.0 g/L albumin | 3.0 g/L albumin | Control group | Blank group |
| Example 3 | Color development and time | Color of the granules changes to light blue after 2 seconds | Color of the granules changes to blue after 2 seconds | Color of the granules changes to blue after 2 seconds | Color of the granules changes to blue after 2 seconds | Color of the granules changes to blue after 2 seconds | No change | No change |
| | Color level Color persistence | / 7 days | +− 7 days | +1 7 days | +2 7 days | +3 7 days | | |
| Example 4 | Color development and time | Color of the granules changes to light blue after 2 seconds | Color of the granules changes to blue after 2 seconds | Color of the granules changes to blue after 2 seconds | Color of the granules changes to blue after 2 seconds | Color of the granules changes to blue after 2 seconds | No change | No change |
| | Color level Color persistence | / 7 days | +− 7 days | +1 7 days | +2 7 days | +3 7 days | | |
| Example 5 | Color development and time | Color of the granules changes to light blue after 2 seconds | Color of the granules changes to blue after 2 seconds | Color of the granules changes to blue after 2 seconds | Color of the granules changes to blue after 2 seconds | Color of the granules changes to blue after 2 seconds | No change | No change |
| | Color level Color persistence | / 7 days | +− 7 days | +1 7 days | +2 7 days | +3 7 days | | |
| Comparison Example 1 | Color development and time | No change | No change | Color of the granules changes to blue after 2 seconds | Color of the granules changes to blue after 2 seconds | Color of the granules changes to blue after 2 seconds | No change | No change |
| | Color level Color persistence | / / | / / | +1 3 days | +2 3 days | +3 3 days | | |

As shown in Table 1, it can be seen that the granules for protein detection in pet urine of the disclosure respond quickly, with prominent color development and long color persistence. When the pet urine contains protein, the granules will turn blue, and when the experimental sample is normal urine or tap water, the color will not change. Therefore, the granules for protein detection of the disclosure can quickly and accurately detect whether the pet urine contains protein, thereby determining the health status of the pet.

It will be obvious to those skilled in the art that changes and modifications may be made, and therefore, the aim in the appended claims is to cover all such changes and modifications.

What is claimed is:

1. A granule for detecting protein in pet urine, the granule comprising: 60-80 parts by weight of silicone particles, 40-50 parts by weight of a filler, 10-20 parts by weight of an adhesive, 1-3 parts by weight of a bacteriostatic agent, 3-5 parts by weight of a deodorant, and 5-10 parts by weight of a tetrabromophenol blue indicator.

2. The granule of claim 1, wherein the silicone particles are modified silicone particles, and are prepared as follows:
   a) ultrasonically cleaning the silicone particles in 30-40° C. water for 10-20 min, and further ultrasonically cleaning in industrial alcohol for 3-5 min, and drying;
   b) soaking the silicone particles treated in a) in N-(2-aminoethyl)-3-aminopropyltrimethoxysilane for 5-10 min, and drying at 50-60° C. in a drying oven; and
   c) soaking the silicone particles treated in b) in a mixed solution comprising polyethylene pyrrolidone, ethyl cellulose, N, N-dimethylformamide, ethyl acetate, and anhydrous ethanol for 10-15 min, and drying at 30-40° C., to yield modified silicone particles.

3. The granule of claim 2, wherein in c), a mass ratio of polyethylene pyrrolidone to ethyl cellulose to N, N-dimethylformamide to ethyl acetate to anhydrous ethanol is 1:0.2:5:1:10.

4. The granule of claim 2, wherein a particle size of the modified silicone particles is 1-2 mm.

5. The granule of claim 1, wherein the filler is modified starch, polyester fiber, acetate fiber, nylon fiber, microcrystalline cellulose, or a mixture thereof.

6. The granule of claim 1, wherein the adhesive is sodium carboxymethyl cellulose, pectin, guar gum, sodium alginate, xanthan gum, or a mixture thereof.

7. The granule of claim 1, wherein the bacteriostatic agent is polyhexamethylene biguanide hydrochloride, sodium benzoate, potassium sorbate, or a mixture thereof.

8. The granule of claim 1, wherein the deodorant is mugwort leaf, grapefruit peel, mulberry leaf, or a mixture thereof.

9. A method for preparing the granule for detecting protein in pet urine of claim 1, the method comprising:
   1) Crushing the silicone particles, the filler, the adhesive, the bacteriostatic agent, and the deodorant to particle size of 1-2 mm, and drying;

2) Dissolving tetrabromophenol blue in 0.1 mol/L NaOH solution, and diluting the NaOH solution containing dissolved tetrabromophenol blue with distilled water until a concentration of tetrabromophenol blue is 0.06% in the NaOH solution, whereby obtaining a tetrabromophenol blue indicator solution;
3) Soaking crushed silicone particles in the tetrabromophenol blue indicator solution obtained in 2) for 30-40 min, and drying; and
4) Mixing the crushed silicone particles treated in 3) and the filler, the adhesive, the bacteriostatic agent, and the deodorant treated in 1), feeding a resulting mixture to a tablet press machine for granulation, to yield flaky granules.

10. The method of claim 9, wherein the complete flaky granules have a diameter of 30 mm, and a thickness of 4 mm.

\* \* \* \* \*